(12) United States Patent
Maurat et al.

(10) Patent No.: US 10,561,585 B2
(45) Date of Patent: Feb. 18, 2020

(54) DENTAL ADHESIVE

(71) Applicant: PRODUITS DENTAIRES PIERRE ROLLAND, Merignac (FR)

(72) Inventors: Vincent Maurat, Pessac (FR); Clemence Pigeron, Bordeaux (FR)

(73) Assignee: PRODUITS DENTAIRES PIERRE ROLLAND, Merignac (FR)

( * ) Notice: Subject to any disclaimer, the term of this patent is extended or adjusted under 35 U.S.C. 154(b) by 0 days.

(21) Appl. No.: 16/151,469

(22) Filed: Oct. 4, 2018

(65) Prior Publication Data

US 2019/0029926 A1 Jan. 31, 2019

Related U.S. Application Data

(63) Continuation of application No. PCT/FR2018/051514, filed on Jun. 22, 2018.

(30) Foreign Application Priority Data

Jun. 23, 2017 (FR) ...................................... 17 55755

(51) Int. Cl.
| | |
|---|---|
| *A61K 6/083* | (2006.01) |
| *A61C 17/20* | (2006.01) |
| *A61K 6/00* | (2020.01) |
| *C08L 33/12* | (2006.01) |
| *C08L 33/20* | (2006.01) |

(52) U.S. Cl.
CPC .............. *A61K 6/083* (2013.01); *A61C 17/20* (2013.01); *A61K 6/0002* (2013.01); *A61K 6/0023* (2013.01); *A61K 6/0026* (2013.01); *A61K 6/0088* (2013.01); *C08L 33/12* (2013.01); *C08L 33/20* (2013.01)

(58) Field of Classification Search
None
See application file for complete search history.

(56) References Cited

U.S. PATENT DOCUMENTS

| | | | | |
|---|---|---|---|---|
| 3,380,831 A | * | 4/1968 | Abraham | ................ C08F 20/20 430/288.1 |
| 3,615,972 A | * | 10/1971 | Morehouse, Jr. | ........ B01J 13/18 156/276 |
| 4,075,138 A | * | 2/1978 | Garner | ................... B01J 13/185 428/402 |

(Continued)

FOREIGN PATENT DOCUMENTS

| | | |
|---|---|---|
| JP | 2007320929 A | 12/2007 |
| TW | 201420122 A | 6/2014 |
| TW | 201442690 A | 11/2014 |

OTHER PUBLICATIONS

French Search Report from FR Application No. 1755755, dated Feb. 21, 2018.

(Continued)

*Primary Examiner* — Peter A Salamon
(74) *Attorney, Agent, or Firm* — Workman Nydegger

(57) ABSTRACT

A dental adhesive comprises at least one polymerizable monomer, a polymerization initiator, and thermo-expandable particles comprising a shell encapsulating an expansion agent, the dental adhesive being characterized in that the shells of the thermo-expandable particles are made of a copolymer of acrylonitrile and methyl methacrylate.

20 Claims, 3 Drawing Sheets

(56) References Cited

U.S. PATENT DOCUMENTS

| | | | | |
|---|---|---|---|---|
| 4,837,200 A * | 6/1989 | Kondo | B41M 5/41 | 428/195.1 |
| 5,176,188 A * | 1/1993 | Quinn | B22C 7/02 | 164/516 |
| 5,356,683 A * | 10/1994 | Egolf | C08J 9/236 | 428/60 |
| 5,360,826 A * | 11/1994 | Egolf | C08J 9/236 | 521/54 |
| 5,364,889 A * | 11/1994 | Quinn | B22C 7/02 | 522/71 |
| 5,418,257 A * | 5/1995 | Weisman | C08J 9/32 | 521/137 |
| 5,453,453 A * | 9/1995 | Lamon | C08J 9/10 | 521/124 |
| 5,520,961 A * | 5/1996 | Lysell | C08L 27/06 | 427/373 |
| 5,804,610 A * | 9/1998 | Hamer | B29B 13/022 | 522/182 |
| 5,814,682 A * | 9/1998 | Rusin | A61K 6/0023 | 433/228.1 |
| 5,827,064 A * | 10/1998 | Bock | A61C 17/20 | 433/216 |
| 6,103,152 A * | 8/2000 | Gehlsen | B29C 44/18 | 264/45.4 |
| 6,172,134 B1 * | 1/2001 | Cooke | C08F 2/44 | 523/176 |
| 6,509,384 B2 * | 1/2003 | Kron | B01J 13/14 | 521/56 |
| 8,987,345 B2 | 3/2015 | Lee et al. | | |
| 2003/0099819 A1 * | 5/2003 | Schroder | B32B 27/30 | 428/212 |
| 2003/0180636 A1 * | 9/2003 | Kanga | B41C 1/05 | 430/18 |
| 2004/0241583 A1 * | 12/2004 | Kanga | B41C 1/05 | 430/300 |
| 2005/0179548 A1 * | 8/2005 | Kittel | G06K 19/07798 | 340/568.2 |
| 2006/0219350 A1 * | 10/2006 | Bain | B29C 65/76 | 156/247 |
| 2007/0207284 A1 * | 9/2007 | McClintic | B32B 7/12 | 428/40.1 |
| 2009/0181250 A1 * | 7/2009 | Zmarsly | B29C 70/606 | 428/352 |
| 2011/0150818 A1 * | 6/2011 | Canfield | A61K 8/895 | 424/78.02 |
| 2011/0260578 A1 * | 10/2011 | Bharti | H01L 41/37 | 310/314 |
| 2012/0029105 A1 * | 2/2012 | Czerwonatis | B29C 44/569 | 521/170 |
| 2012/0295077 A1 * | 11/2012 | Ficek | G03F 7/002 | 428/195.1 |
| 2014/0148526 A1 * | 5/2014 | Lee | A61K 6/0023 | 523/118 |
| 2014/0235747 A1 * | 8/2014 | Rundlett | G03F 7/002 | 522/170 |
| 2014/0370317 A1 * | 12/2014 | Nabuurs | C08F 220/14 | 428/522 |
| 2016/0035340 A1 * | 2/2016 | Miyawaki | G10K 11/162 | 252/62 |
| 2019/0029926 A1 * | 1/2019 | Maurat | A61C 17/20 | |

OTHER PUBLICATIONS

Taiwanese Office Action for TW Application No. 107121459, dated Apr. 19, 2019.

\* cited by examiner

DENTAL ADHESIVE

BACKGROUND OF THE INVENTION

Orthodontic adhesives serve to fasten an orthodontic appliance on the surface of a tooth.

Orthodontic adhesives typically comprise one or more polymerizable monomers of the acrylate or methacrylate type, together with a polymerization initiator.

An orthodontic appliance is durably fastened to the tooth by causing the monomers present in the adhesive to polymerized, e.g. under irradiation from blue light.

Once the orthodontic treatment has been performed, the orthodontic appliance needs to be removed from the surface of the tooth.

To do that, the appliance can be removed mechanically by using forceps designed for that purpose. That method is relatively rough and can lead to lesions in the enamel. The use of forceps can be painful, or even traumatic for the patient. The adhesive is not necessarily removed in full, and residues may remain on the teeth, thus requiring the use of a dental bur to remove them. That treatment can also lead to additional damage to the enamel.

In order to avoid using that mechanical method for unsticking the orthodontic appliance, application JP 2007/320929 proposes an orthodontic adhesive that incorporates thermo-expandable particles. Each thermo-expandable particle is in the form of a shell encapsulating an expansion agent, such as butane. Under the effect of an increase in temperature, the expansion agent contained in the shell expands, thereby causing the shell to expand and the volume of the particles to increase.

Application JP 2007/320929 proposes performing unsticking, no longer by using forceps, but by heating the adhesive to a temperature that is relatively high in order to expand the thermo-expandable particles, thereby causing the polymer lattice to break. Nevertheless, the use of a heater member applying a relatively high temperature can lead to discomfort, and even to a risk of burning for the patient being treated.

Removing other types of dental adhesive is likewise not possible in a manner that is entirely satisfactory. On this topic, mention may be made of removing dental cements that are used for temporarily plugging a cavity formed inside a tooth, e.g. after removing caries. Such dental cements are usually removed mechanically using a dental bur. That method can lead to damaging a patient's dental tissue.

OBJECT AND SUMMARY OF THE INVENTION

The present invention overcomes the drawbacks of the prior art techniques.

In a first aspect, the invention provides a dental adhesive comprising at least one polymerizable monomer, a polymerization initiator, and thermo-expandable particles comprising a shell encapsulating an expansion agent, the dental adhesive being remarkable in that the shells of the thermo-expandable particles are made of a copolymer of acrylonitrile and methyl methacrylate.

The inventors have been made two main observations during their work.

Firstly, they have observed that using ultrasound vibration serves to expand the thermo-expandable particles, thereby breaking the polymer lattice of the adhesive and reducing its adhesive power. This effect occurs regardless of the nature of the shells of the thermo-expandable particles. As a result, applying ultrasound makes it possible to obtain effective and comfortable unsticking of the dental adhesive while producing heating that is limited, thereby reducing the risk of burning the patient.

Furthermore, it has been observed that using specific thermo-expandable particles having a shell made of a copolymer of acrylonitrile and methyl methacrylate serves to still further reduce the heating during the application of ultrasound, insofar as expansion of those particles corresponds to a transformation that is endothermic.

The invention thus makes it possible, at the end of the treatment, to unstick the dental adhesive in a manner that is simple and more comfortable for the patient, in particular by reducing the risk of burning and of damaging dental tissue.

In an embodiment, the content by weight of thermo-expandable particles is in the range 10% to 45%.

A content by weight of thermo-expandable particles that is greater than or equal to 10% serves to still further facilitate unsticking the adhesive using ultrasound. Limiting this content by weight to not more than 45% also makes it possible to ensure good fastening by the adhesive while the treatment is taking place.

In particular, the content by weight of thermo-expandable particles may be in the range 10% to 20%.

In an embodiment, the polymerizable monomer(s) is/are selected from: bisphenol A glycidyl dimethacrylate (Bis-GMA); triethylene glycol dimethacrylate (TEGDMA); hydroxethyl methacrylate (HEMA); polyethylene glycol dimethacrylate (PEGDMA); diurethane dimethacrylate (DUDMA); and mixtures of such monomers.

The invention also provides a method of unsticking a polymerized dental adhesive fastened to the surface of a tooth, said polymerized adhesive comprising at least a resin and thermo-expandable particles, the method being remarkable in that the polymerized adhesive is unstuck by applying ultrasound vibration to the polymerized adhesive.

Such a method enables a polymerized dental adhesive to be unstuck in a manner that is comfortable for the patient, in particular by reducing the risk of burning and of damaging dental tissue.

The polymerized adhesive may be obtained by polymerizing the above-described adhesive.

Thus, the thermo-expandable particles may have a shell made of a copolymer of acrylonitrile and methyl methacrylate encapsulating an expansion agent.

As mentioned above, the use of the specific thermo-expandable particles serves to still further limit heating during unsticking with ultrasound.

In particular, the frequency of the ultrasound vibration applied may lie in the range 26 kilohertz (kHz) to 36 kHz.

The above-described dental adhesive may be used in various dental applications.

Thus, in a first example, the dental adhesive may be an orthodontic adhesive and it may be used for fastening an orthodontic appliance to the surface of a tooth.

Under such circumstances, at the end of the orthodontic treatment, the orthodontic appliance is unstuck by applying ultrasound vibration to the polymerized adhesive. Thus, in this first example, the method is such that a dental appliance is fastened to the surface of the tooth by the polymerized dental adhesive, and such that the appliance is unstuck by applying ultrasound vibration.

In particular, the application of the ultrasound vibration may be continued, after the orthodontic appliance has been unstuck, in order to unstick a residue of polymerized dental adhesive adhering to the surface of the tooth.

In a second example, the dental adhesive may be a dental cement used for closing a cavity formed in a tooth.

Thus, in this second example, the method is such that the polymerized dental adhesive is a dental cement closing a cavity in the tooth, and such that the cavity is unplugged by applying ultrasound vibration.

BRIEF DESCRIPTION OF THE DRAWINGS

Other characteristics and advantages of the invention appear from the following description given by way of non-limiting example and with reference to the accompanying drawings, in which.

DETAILED DESCRIPTION OF EMBODIMENTS

Figure 1:
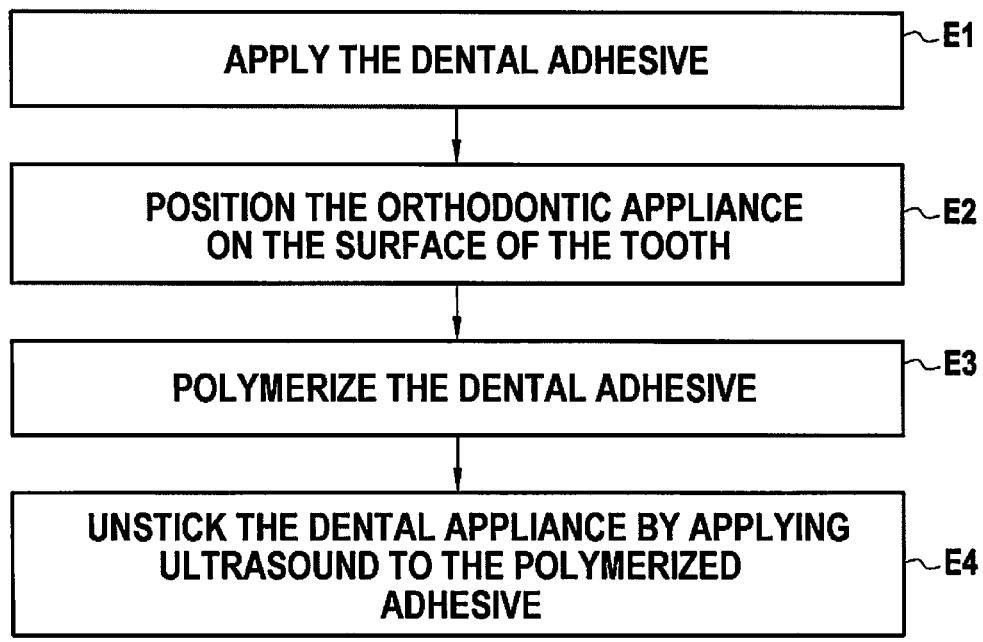
FIG. 1 is a flow chart showing the various steps performed in order to stick and then unstick an orthodontic appliance to and from the surface of a tooth, as can be performed in the context of an example of the invention.

With reference to FIGS. 1 to 5, there follows a description of an example of the invention in which adhesive is used for fastening an orthodontic appliance to the surface of a tooth.

In order to stick on an orthodontic appliance, a layer of adhesive is initially applied to the orthodontic appliance and/or to a surface of the tooth that is to receive the appliance (step E1). Conventional preliminary treatment of cleaning and applying mordant to the surface of the tooth may be performed beforehand.

The adhesive comprises at least one polymerizable monomer and a polymerization initiator. Said at least one polymerizable monomer may be an acrylate or methacrylate monomer. The adhesive may have a single polymerizable monomer or it may comprise a mixture of a plurality of different polymerizable monomers.

The adhesive used in the context of the invention further comprises thermo-expandable particles. Each thermo-expandable particle presents a shell encapsulating an expansion agent.

In preferred manner, the shell is made of a copolymer of acrylonitrile and methyl methacrylate (AN/MMA). Particles presenting such a shell are available under the references Expancel FG52 DU 80 or Expancel 031 DU 40 from the supplier AkzoNobel.

In a variant, it is possible to use thermo-expandable particles having a shell made of a copolymer of vinylidene chloride and acrylonitrile ($VCl_2$/AN). Particles presenting such a shell are available under the reference Microsphere☐ F-30 from the supplier Matsumoto.

By way of example, the expansion agent may be a hydrocarbon such as butane. The expansion agent may be in the gaseous state.

The mean size (D50) of the thermo-expandable particles may lie in the range 6 micrometers ($\mu$m) to 80 $\mu$m.

The adhesive may also include a coupling agent such as an organosilane. The adhesive may also include at least one filler, such as silica.

In particular, the adhesive may comprise:

said at least one polymerizable monomer at a content by weight lying in the range 24% to 84.8%, e.g. in the range 57.5% to 79.4%;

the polymerization initiator at a content by weight lying in the range 0.1% to 1%, e.g. in the range 0.1% to 0.5%; and the thermo-expandable particles at a content by weight lying in the range 10% to 45%, e.g. in the range 10% to 20%; and optionally a filler at a content by weight lying in the range 5% to 25%, e.g. in the range 10% to 20%; and optionally the coupling agent at a content by weight lying in the range 0.01% to 5%, e.g. in the range 0.5% to 2%.

Once the adhesive has been applied, the orthodontic appliance is then positioned on the surface of the tooth (step E2).

The orthodontic appliance may be an orthodontic bracket to which an orthodontic wire is to be fastened. In a variant, the orthodontic appliance may be an orthodontic ring or a retaining arch, for example. The orthodontic appliance may be made of metallic, ceramic, or composite material.

Once the orthodontic appliance has been put into position, the monomer(s) is/are polymerized, e.g. under the effect of light irradiation (step E3). The polymerized adhesive that is obtained comprises a resin that results from polymerizing the polymerizable monomer(s). The polymerization is initiated by the polymerization initiator. The orthodontic appliance is fastened to the surface of the tooth by the polymerized adhesive. It is possible to fasten a plurality of orthodontic brackets on a patient's teeth. Once the orthodontic brackets are in position, an orthodontic wire can be fastened using those brackets in order to perform the desired orthodontic treatment.

At the end of the orthodontic treatment, the orthodontic appliance(s) is/are unstuck by applying ultrasound to the polymerized adhesive layer (step E4).

To perform this step, an ultrasound applicator, such as an ultrasound tip, is moved up to the polymerized adhesive. As an example of a suitable ultrasound applicator, mention may be made of the No. 10P insert sold by the supplier Satelec. The frequency of the ultrasound applied for performing the unsticking may lie in the range 26 kHz to 36 kHz.

Figure 9:
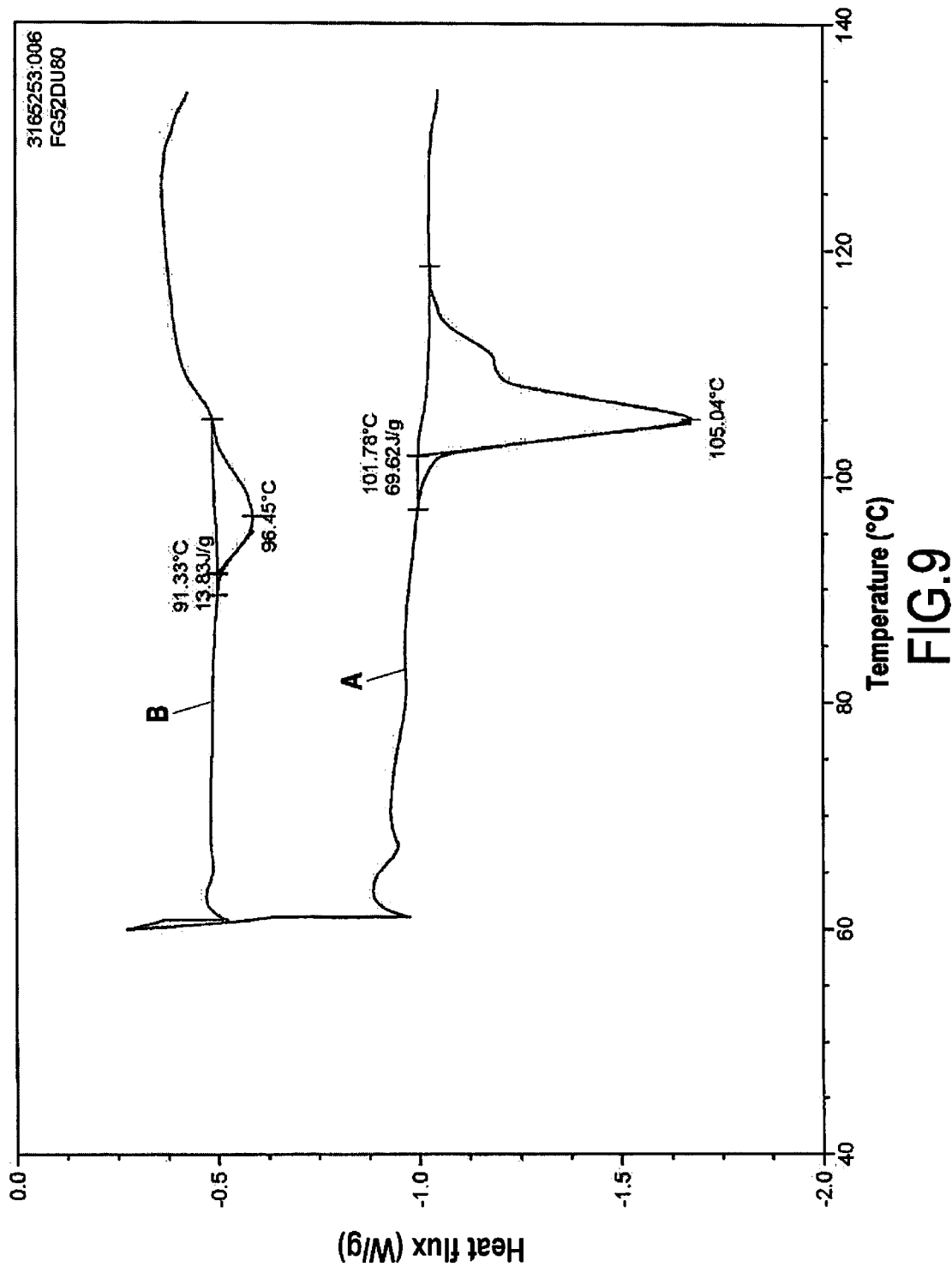
FIG. 9 shows the results obtained by differential scanning calorimetry comparing the endothermic nature of the expansion of two types of thermo-expandable particles.

The use of thermo-expandable particles, each having a shell made of AN/MMA copolymer is preferred. FIG. 9 shows an experimental result obtained by differential scanning calorimetry (DSC), which shows that expanding AN/MMA particles (curve A) is significantly more endothermic than is expanding $VCl_2$/AN particles (curve B): 69.62 joules per gram (J/g) as compared with 13.83 J/g. That test was performed using AN/MMA particles of reference Expancel FG52 DU 80 and $VCl_2$/AN particles of reference Microsphere☐ F-30 from the supplier Matsumoto. During the test, temperature was raised at a rate of 3° C./per minute (min) from 60° C. to 140° C. During thermal activation in the DSC test, the AN/MMA particles expanded at a temperature a little higher than that at which the VCl$_2$/AN particles expanded. Nevertheless, when the particles are expanded by applying ultrasound vibration, as in the context of the invention, there is no need to raise the AN/MMA particles to a higher temperature, and the heating produced during unsticking is significantly more limited with AN/MMA particles than with VCl$_2$/AN particles. The use of AN/MMA particles thus makes it possible to ensure that unsticking the adhesive using ultrasound is even more comfortable than when using the VCl$_2$/AN particles.

Figure 2:
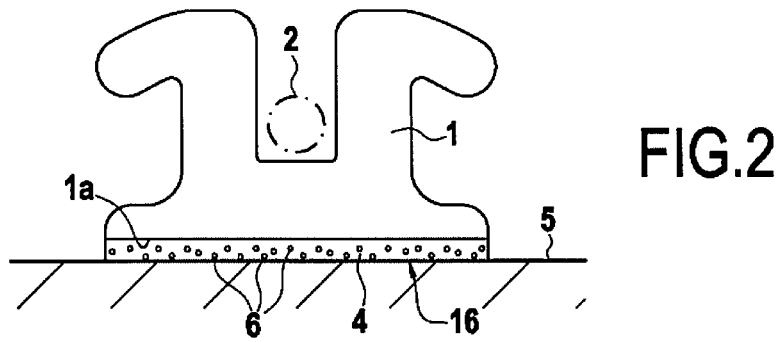
FIG. 2 is a diagram showing an orthodontic appliance fastened to the surface of a tooth.

FIG. 2 shows the performance of orthodontic treatment in which an orthodontic bracket 1 is fastened to the surface 5 of a tooth.

The bracket 1 is caused to adhere to the surface 5 by a layer of polymerized adhesive 16 that comprises the resin 4 and the thermo-expandable particles 6.

The layer of polymerized adhesive 16 is present between the back wall 1a of the bracket 1 and the surface 5. An orthodontic wire 2 is fastened to the bracket 1 in order to perform the orthodontic treatment.

Figure 3:
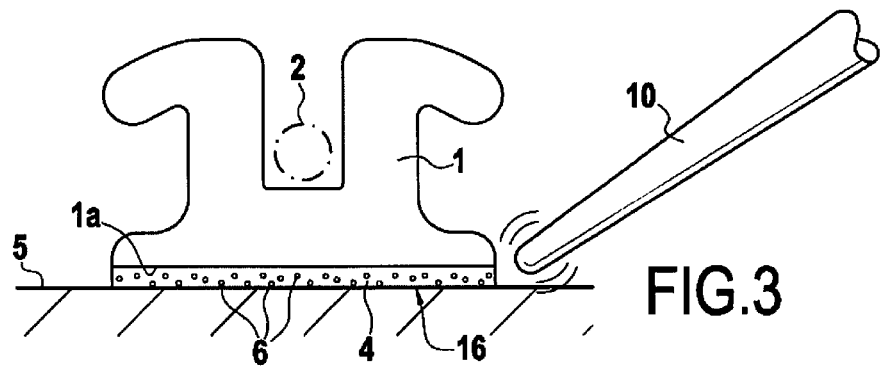
FIG. 3 is a diagram showing ultrasound being applied to unstick the orthodontic appliance from the surface of the tooth in the context of a first example of the method of the invention.
Figure 4:
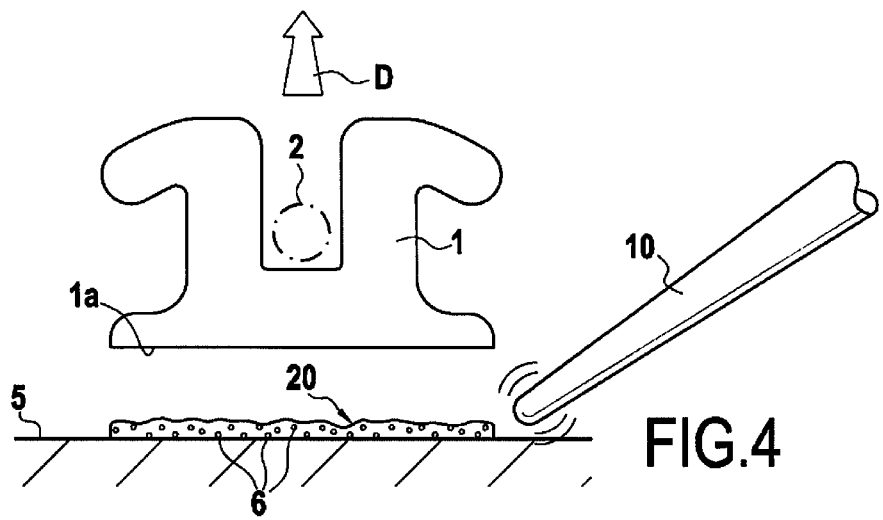
FIG. 4 is a diagram showing the application of ultrasound to unstick the adhesive residue after the orthodontic appliance has been unstuck, in the context of the first example of the method of the invention.

FIGS. 3 and 4 show the bracket 1 being unstuck at the end of the orthodontic treatment.

An ultrasound tip 10 is moved up to the polymerized adhesive 16 and it vibrates at an ultrasound frequency (FIG. 3). The thermo-expandable particles 6 expand under that effect, thereby breaking the polymer lattice of the adhesive. The ultrasound tip 10 may be provided with a nozzle for delivering water in order to enhance elimination of the adhesive 20 from the surface of the tooth.

The operator can then easily unstick the bracket 1 from the surface 5 of the tooth (arrow D in FIG. 4) with limited heating and without risk of damaging dental tissue.

It is possible for a residue 20 of adhesive to remain on the surface 5 of the tooth after unsticking the bracket 1, as shown in FIG. 4.

Figure 5:
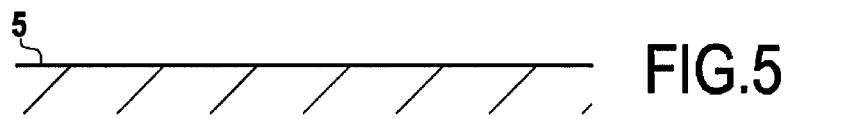
FIG. 5 is a diagram showing the surface state of the tooth as obtained after eliminating the adhesive residue in the context of the first example of the method of the invention.

Advantageously, the application of ultrasound can be continued after the bracket 1 has been unstuck in order to eliminate the residue 20. An adhesive-free surface state 5 is then obtained for the tooth, as shown in FIG. 5.

The use of ultrasound serves advantageously to avoid using a dental bur in order to eliminate the adhesive residue, thereby still further limiting the risk of damaging dental tissue.

Figure 6:
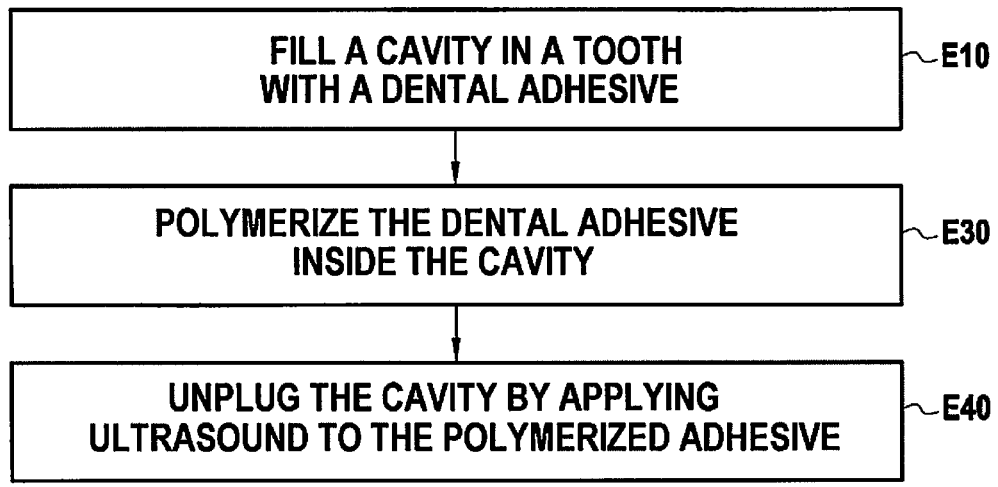
FIG. 6 is a flow chart showing various steps performed in order to plug temporarily a cavity formed inside a tooth and subsequently unplug it, which steps can be performed in the context of a variant of the invention.
Figures 7, 8:
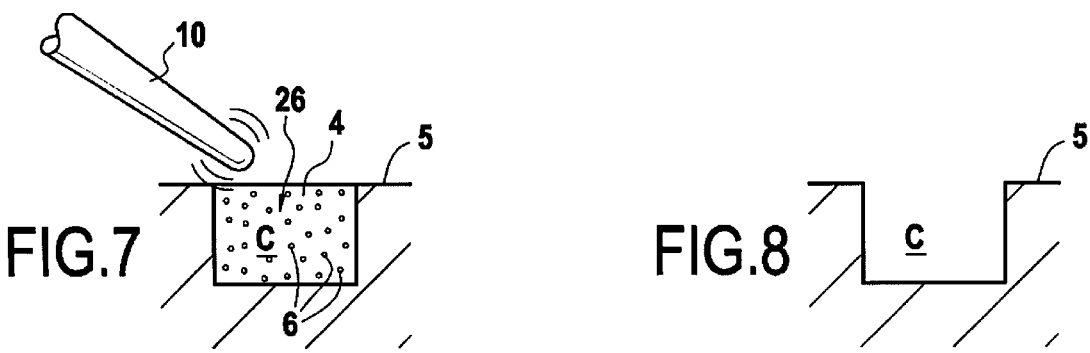
FIG. 7 is a diagram showing the application of ultrasound to unplug a cavity closed by a dental cement in the context of a second example of the method of the invention.
FIG. 8 is a diagram showing the unplugged cavity obtained after eliminating the dental cement.

With reference to FIGS. 6 to 8, there follows a description of a variant implementation in which the adhesive is a dental cement used for temporarily plugging a cavity present in a tooth. By way of example, such a dental cement may be used for plugging the cavity that results from removing caries, while waiting for subsequent treatment.

With reference to FIG. 6, the measured example described herein comprises filling the cavity with a dental cement constituted by the above-described dental adhesive (step E10).

The adhesive is then polymerized as described above so as to obtain polymerized dental cement inside the cavity (step E30). The polymerized dental cement thus serves to close the cavity for the desired duration while waiting for subsequent dental treatment.

At the desired time, the polymerized dental cement is eliminated by applying ultrasound. In a manner similar to that described above, applying ultrasound leads to the thermo-expandable particles expanding and to the dental cement becoming unstuck so as to unplug the cavity (step E40).

Unplugging of the cavity is described with reference to FIGS. 7 and 8.

FIG. 7 shows the presence of the ultrasound tip 10 in the vicinity of the polymerized dental cement 26 closing the cavity C. As described above, the cement 26 comprises the resin 4 and the thermo-expandable particles 6. The characteristics described above when describing the orthodontic adhesive, e.g. the contents of the various ingredients, are applicable to this implementation.

As a result of the thermo-expandable particles 6 expanding under the effect of ultrasounds, the cement 26 becomes unstuck and is eliminated away from the cavity C.

This treatment gives rise to the unplugged cavity C as shown in FIG. 8.

This method of unplugging a cavity closed by dental cement by using ultrasound serves advantageously to avoid using a dental bur, thereby limiting the risk of damaging dental tissue.

The invention applies to treating natural teeth or artificial teeth.

Example

An orthodontic adhesive having the composition set out in Table 1 below was prepared. The proportions of each of the ingredients are given as percentages by weight.

TABLE 1

| Ingredients | |
|---|---|
| BIS-GMA | 48.68% |
| TEGDMA | 20.87% |
| Expancel FG52 DU 80 | 15.00% |
| Photo-initiator system | 0.45% |
| Filler (modified silica) | 14.00% |
| Gelling agent (colloidal silica) | 1.00% |
| TOTAL | 100.00% |

In order to make the orthodontic adhesive having the composition set out in Table 1 above, the following operating protocol was implemented.

A first mixture of BIS-GMA and TEGDMA monomers was made using a turbotest type stirrer in a beaker. The total duration of the mixing stage was 15 min. Stirring was performed at a speed of 200 revolutions per minute (rpm).

The photo-initiator system was incorporated in the first mixture and stirring was performed using the "turbotest" stirrer for 40 min. The photo-initiator system was a camphoroquinone and tertiary amine system. The beaker was surrounded in aluminum foil in order to avoid exposure to light. Stirring was performed at a speed of 180 rpm. The content of the mixture obtained in that way was then transferred into the vessel of a planetary mixer and mixed under a vacuum for 5 min. A second mixture was thus obtained.

The filler was added to the second mixture and stirring was performed for about 10 min in order to obtain a paste. An additional stage of stirring the resulting paste was then performed under a vacuum for 5 min. A third mixture was thus obtained.

The Expancel FG52 DU 80 thermo-expandable particles were then added to the third mixture. First stirring was performed for 5 min in order to incorporate the particles completely, followed by second stirring under a vacuum for 5 min. A fourth mixture was thus obtained.

The gelling agent was then added to the fourth mixture. Stirring was performed for 2 min in order to incorporate the gelling agent completely. Stirring under a vacuum was then performed for 8 min.

The orthodontic adhesive as finally obtained had a weight of 91.91 grams (g). The resulting adhesive was in the form of a pale yellow paste that was sticky and dense.

The orthodontic adhesive as obtained in that way was then used for sticking an orthodontic bracket to the surface of a tooth in order to evaluate the possibility of unsticking the bracket with ultrasound. The following operating protocol was performed:

cleaning the surface of each tooth;
applying mordant to the same surfaces in the form of a gel that was put into place and left in place for 30 seconds (s) to 60 s;
eliminating the mordant gel, rinsing, and drying the surface to which it had been applied; using a syringe to apply the orthodontic adhesive to the back wall of the orthodontic bracket for fastening;
positioning the bracket on the surface of the teeth and adjusting its position using a hook;
removing excess adhesive around the base of the bracket without moving it;
using blue light irradiation from a "Mini LED" device sold by the supplier Satelec to polymerize the orthodontic adhesive over a period of 5 s to 25 s above each interproximal side;
repeating the above-described operations for the entire dental arch to be treated; and
positioning orthodontic wire after fastening the last bracket.

Ultrasound was subsequently applied around each bracket at the interface between the adhesive and the bracket using a 10P insert sold by the supplier Satelec. The brackets were thus unstuck easily from the surfaces of the teeth with limited heating and without damaging dental tissue.

After removing the orthodontic wire and the brackets, the teeth that still presented a deposit of adhesive were cleaned by applying ultrasound until all of the residue had been eliminated.

The term "lying in the range . . . to . . . " should be understood as including the bounds.

The invention claimed is:

1. A dental adhesive comprising:
   at least one polymerizable monomer,
   a polymerization initiator, and
   thermo-expandable particles comprising a shell encapsulating an expansion agent, wherein the shells of the thermo-expandable particles are made of a copolymer of acrylonitrile and methyl methacrylate,
   wherein the polymerizable monomer(s) is/are selected from the group consisting of:
   bisphenol A glycidyl dimethacrylate; triethylene glycol dimethacrylate; polyethylene glycol dimethacrylate; diurethane dimethacrylate; and mixtures of such monomers, and
   wherein upon polymerization the dental adhesive adheres to a surface of a tooth so as to fasten an orthodontic appliance to the surface of the tooth or to close a cavity in the tooth.

2. The adhesive according to claim 1, wherein the content by weight of thermo-expandable particles is in the range 10% to 45%.

3. The adhesive according to claim 2, wherein the content by weight of thermo-expandable particles is in the range 10% to 20%.

4. The adhesive according to claim 1, wherein the polymerizable monomer(s) is/are selected from the group consisting of: bisphenol A glycidyl dimethacrylate; triethylene glycol dimethacrylate.

5. A method of unsticking a polymerized dental adhesive fastened to the surface of a tooth, said polymerized adhesive comprising at least a resin and thermo-expandable particles having a shell formed by a copolymer of acrylonitrile and methyl methacrylate encapsulating an expansion agent, wherein the polymerized adhesive is unstuck by applying ultrasound vibration to the polymerized adhesive.

6. The method according to claim 5, wherein the frequency of the ultrasound vibration applied lies in the range 26 kHz to 36 kHz.

7. The method according to claim 5, wherein a dental appliance is fastened to the surface of the tooth by the polymerized dental adhesive, and wherein the appliance is unstuck by applying ultrasound vibration.

8. The method according to claim 7, wherein the application of the ultrasound vibration is continued, after the orthodontic appliance has been unstuck, in order to unstick a residue of polymerized dental adhesive present at the surface of the tooth.

9. The method according to claim 5, wherein the polymerized dental adhesive is a dental cement closing a cavity in the tooth, and wherein the cavity is unplugged by applying ultrasound vibration.

10. The method according to claim 5, wherein the content by weight of thermo-expandable particles is in the range 10% to 45%.

11. The method according to claim 10, wherein the content by weight of thermo-expandable particles is in the range 10% to 20%.

12. The method according to claim 5, wherein the polymerizable monomer(s) includes bisphenol A glycidyl dimethacrylate; triethylene glycol dimethacrylate; hydroxethyl methacrylate; polyethylene glycol dimethacrylate; diurethane dimethacrylate; or mixtures of such monomers.

13. A method of unsticking a polymerized dental adhesive fastened to the surface of a tooth, said polymerized dental adhesive comprising at least a resin and thermo-expandable particles having a shell formed by a copolymer of acrylonitrile and methyl methacrylate encapsulating an expansion agent, said method comprising applying ultrasound vibration to the polymerized dental adhesive.

14. The method according to claim 13, wherein the frequency of the ultrasound vibration applied lies in the range 26 kHz to 36 kHz.

15. The method according to claim 13, wherein a dental appliance is fastened to the surface of the tooth by the polymerized dental adhesive, and wherein the appliance is unstuck by applying ultrasound vibration.

16. The method according to claim 15, wherein the application of the ultrasound vibration is continued, after the orthodontic appliance has been unstuck, in order to unstick a residue of polymerized dental adhesive present at the surface of the tooth.

17. The method according to claim 13, wherein the polymerized dental adhesive is a dental cement closing a cavity in the tooth, and wherein the cavity is unplugged by applying ultrasound vibration.

18. The method according to claim 13, wherein the content by weight of thermo-expandable particles is in the range 10% to 45%.

19. The method according to claim 13, wherein the polymerizable monomer(s) includes bisphenol A glycidyl dimethacrylate; triethylene glycol dimethacrylate; hydroxethyl methacrylate; polyethylene glycol dimethacrylate; diurethane dimethacrylate; or mixtures of such monomers.

20. The dental adhesive according to claim 1, wherein the polymerizable monomer is a mixture of bisphenol A glycidyl dimethacrylate and triethylene glycol dimethacrylate.

* * * * *